United States Patent [19]

Lai

[11] Patent Number: 4,523,032

[45] Date of Patent: Jun. 11, 1985

[54] 3,5-DIALKYL-4-HYDROXYPHENYL-SUBSTITUTED ACETIC ACIDS

[75] Inventor: John T. Lai, Broadview Hgts., Ohio

[73] Assignee: The B. F. Goodrich Company, Akron, Ohio

[21] Appl. No.: 549,034

[22] Filed: Nov. 7, 1983

[51] Int. Cl.³ .............................................. C07C 65/01
[52] U.S. Cl. ...................................... 562/478; 562/469
[58] Field of Search ................................. 562/478, 469

[56] References Cited

U.S. PATENT DOCUMENTS 3,455,995  7/1969  Knell .................................... 560/78

Primary Examiner—Paul J. Killos
Attorney, Agent, or Firm—J. Hughes Powell, Jr.; Alan A. Csontos

[57] ABSTRACT

3,5-Dialkyl-4-hydroxyphenyl-substituted acetic acids are prepared by reacting a 2,6-dialkylphenol with a haloform, a ketone and an alkali metal hydroxide. These 3,5-dialkyl-4-hydroxyphenyl-substituted acetic acids are also useful as stabilizers and in the preparation of derivatives thereof such as esters and the like.

16 Claims, No Drawings

3,5-DIALKYL-4-HYDROXYPHENYL-SUBSTITUTED ACETIC ACIDS

SUMMARY OF THE INVENTION 3,5-dialkyl-4-hydroxyphenyl-substituted acetic acids are prepared by reacting a 2,6-dialkylphenol with a haloform, a ketone and an alkali metal hydroxide.

DETAILED DESCRIPTION

The novel 3,5-dialkyl-4-hydroxyphenyl-substituted acetic acids of this invention have the general formula

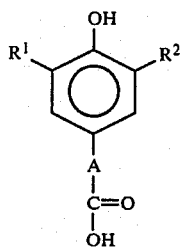

wherein $R^1$ and $R^2$ are alkyl and cycloalkyl groups containing 1 to 12 carbon atoms, alkylcycloalkyl and aryl or alkaryl groups wherein the alkyl groups contain 1 to 8 carbon atoms, and the aryl groups are normally phenyl or naphthyl. Preferably $R^1$ is an alkyl group containing 1 to 8 carbon atoms, $C_1$–$C_8$ and $R^2$ is an alkyl group containing 1 to 5 carbon atoms, and more preferably at least one of $R^1$ or $R^2$ is a t-alkyl group including t-butyl and t-amyl; and A is (1) an alkyl group of the formula

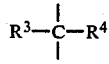

wherein $R^3$ and $R^4$ are alkyl groups containing 1 to 18 carbon atoms, $C_1$–$C_{18}$, preferably alkyl groups containing 1 to 8 carbon atoms, $C_1$–$C_8$ and more preferably 1 to 4 carbon atoms; or (2) a cycloalkyl group containing 5 to 12 carbon atoms, including for example those derived from cyclohexanone, cycloheptanone, dicyclohexyl ketone, alkyl aryl ketones wherein the alkyl groups contain 1 to 8 carbon atoms and the aryl preferably is phenyl or naphthyl, and the like.

These 3,5-dialkyl-4-hydroxyphenyl-substituted acetic acids are prepared by a novel process by reacting a 2,6-di-alkylphenol with an aliphatic, cycloaliphatic or alkaryl ketone with a haloform in the presence of alkali metal hydroxide. An organic solvent may be used, or large amounts of the ketone reactant may be employed. The acid is isolated in excellent yields by treating the reaction product with an aqueous acid solution and crystallizing the reaction product.

Typical 2,6-dialkyl phenols used have the formula

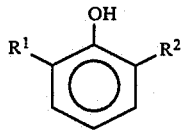

wherein $R^1$ and $R^2$ have the meanings set forth above, including 2-methyl-6-t-butylphenol, 2-ethyl-6-t-butylphenol, 2-propyl-6-t-butylphenol, 2-isopropyl-6-t-butylphenol, 2-n-butyl-6-t-butyphenol, 2,6-di-t-butyphenol, 2-n-amyl-6-t-butylphenol, 2-isoamyl-6-t-butylphenol, 2-hexyl-6-t-butylphenol, 2-heptyl-6-t-butylphenol, 2-isooctyl-6-t-butylphenol, 2-isopropyl-6-t-butylphenol, 2-n-butyl-6-isopropylphenol, 2-isoamyl-6-ethylphenol, 2-isoamyl-6-methylphenol, 2-isooctyl-6-methylphenol, 2-isooctyl-6-ethylphenol, 2-isooctyl-n-propylphenol, 2-isooctyl-6-n-hexylphenol, and the like.

The ketones used include dialkyl ketones, cycloalkanones, alkylcycloalkanones, and alkaryl ketones. Typical ketones that may be used in the novel process to make the new 3,5-dialkyl-4-hydroxyphenyl-substituted acetic acids of the invention are alkyl ketones of the formula

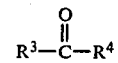

wherein $R^3$ and $R^4$ are alkyl radicals containing 1 to 18 carbon atoms, preferably 1 to 8 carbon atoms, $C_1$–$C_8$, including for example acetone, methyl ethyl ketone, methyl n-propyl ketone, diethyl ketone, 2-hexanone, 3-hexanone, di-n-propyl ketone, 2-octanone, metheyl isobutyl ketone, and the like. Also useful are the cycloalkane ketones containing 5 to 12 carbon atoms such as cyclobutanone, cyclopentanone, cyclohexanone, cycloheptanone, cyclooctanone, 2-methylcyclopentanone, 2-methylcyclohexanone, dicyclohexyl ketone, alkaryl ketones when the alkyl group contains 1 to 4 carbon atoms such as acetophenone, o-methoxyacetophenone, p-chloroacetophenone, and the like; in amounts from at least about 1 mole of ketone per mole of 2,6-dialkylphenol, up to amounts sufficient for the ketones to be the solvent of the reaction, 10 moles or more. No more than about two moles is preferred when the ketone is a reactant only. Use of less than 1 mole reduces the product yield, and more than about 2 moles is unnecessary unless the ketone is the solvent.

The other essential reactants for the novel process of this invention include the alkali metal hydroxide in powder form, or in solution, including sodium hydroxide and potassium hydroxide. Preferably, a molar excess of the alkali metal hydroxide is used in relation to the amount of 2,6-dialkylphenol present. Normally from about 4 moles of alkali metal hydroxide per mole of 2,6-dialkylphenol up to 10 or more moles may be used, but the amount used preferably is about 4 to about 8 moles of hydroxide per mole of 2,6-dialkylphenol. Use of less than about 4 moles will reduce the yield of desired product.

The haloform, such as chloroform, is also used in a molar ratio of at least about one mole per mole of 2,6-dialkylphenol used, but preferably a slight molar excess is used up to about a 50 weight percent molar excess, i.e., 1.5 mole per mole of 2,6-dialkylphenol. While larger amounts may be used, there is no advantage realized, and lesser amounts will decrease the ultimate yield of the desired product. Bromoform may be substituted for the chloroform and excellent results will be obtained.

Although a catalyst is not absolutely essential, it is preferably used in the reaction. These catalysts are typically onium salts, that is, quarternary compounds of ions derived from Groups VA and VIA elements that generally have the formula $(R_4Y)+X-$ wherein R are monovalent hydrocarbon radicals including alkyl, aryl, alkaryl, cycloalkyl and like radicals, Y is phosphorous or nitrogen and X is a halide, hydrosulfate, or like ions. Benzyltriethylammonium chloride has been found to be useful in amounts in the range of about 0.01 to about 0.1 mole of benzyltriethylammonium chloride per mole of 2,6-dialkylphenol used. Larger amounts are not necessary and lower amounts may be used if the reaction rate obtained is satisfactory. Other catalysts useful in the process that may be used include tetraalkyl ammonium salts such as tetrabutyl ammonium bromide, tetrabutylammonium hydrogensulfate, methyl trioctylammonium chloride, tetraalkyl phosphonium salts such as tetrabutyl phosphonium bromide, cetyltributyl phosphonium bromide, and the like.

The solvent used may be any polar organic solvent, including an excess of the ketone used in place of an added solvent. Typical solvents that may be used include methylene chloride, tetrahydrofuran, diethyl ether, dibutyl ether, dimethyl sulfone, 1,4-dioxane, carbon tetrachloride, toluene, and the like. The amounts of solvent used will vary from about 5 moles to 100 moles per mole of 2,6-dialkylphenol used. As has been stated, the solvent may be eliminated if an excess of the reactant ketone is used. In this case, the amount of ketone used, based on the moles of 2,6-dialkylphenol used may be from about 5 to about 20, preferably about 7.5 to 15 moles per mole of 2,6-dialkylphenol.

While the reactants may be added in any order, it is preferred that the alkali metal hydroxide be added last, over a period of time to control the exothermic reaction and preferably maintain the reaction below 30° C., preferably below about 10° C. The reaction temperature may be varied from about 0° C. to about 30° C., but preferably is conducted from about 0° C. to 10° C. The reaction time normally will vary from about 5 to about 15 hours.

The 3,5-dialkyl-4-hydroxyphenol-substituted acetic acids are readily isolated from the reaction mixture by adding sufficient aqueous inorganic acid, including hydrochloric or sulfuric acid, to the reaction mixture to isolate the acid, most of which is in the organic layer that forms. The aqueous layer is extracted with solvent to remove all traces of the acid, and this is added to the other organic layer and this mixture is dried with a desiccant such as anhydrous sodium sulfate, and heated to dryness. This product may be recrystallized if desired.

The practice of the invention is demonstrated in the following Examples. The structures of the 3,5-dialkyl-4-hydroxyphenyl-substituted acetic acids of the following Examples were confirmed by infrared and nuclear magnetic resonance spectra. Molecular weights were determined and confirmed by field desorption mass spectra (FD/MS). Elemental analysis of carbon and hydrogen was done and the amounts found were consistent with the formulas of the materials.

EXAMPLE 1

2-(3,5-Di-t-butyl-4-hydroxyphenyl)-2-methyl propanoic acid 0.1 mole of 2,6-di-t-butylphenol, 0.12 moles of chloroform, 0.15 mole of acetone and 0.003 mole of benzyltriethylammonium chloride were mixed with 100 ml of methylene chloride in a 500 ml three-neck reactor having a circulating cold bath. While stirring, 0.5 mole of powdered sodium hydroxide was added in small portions during a 30 minute period. After this addition, the reaction temperature was slowly raised to 10° C. and stirred overnight. 200 ml of 4N HCl was then added slowly and the resulting 2 layers were separated. The aqueous layer was extracted twice with 50 ml of methylene chloride. The combined organic layers were dried with sodium sulfate and concentrated. The residue was washed with hexanes to obtain straw-colored crystals in >90% yield. The product may be recrystallized from aqueous ethanol to afford white solid. The melting point was 210°–214° C.; the molecular weight 292; carbon-calculated 73.93%, found 74.16%; hydrogen-calculated 9.65%, found 9.72%.

EXAMPLE II 2-(3,5-Di-t-butyl-4-hydroxyphenyl)-2-methylbutanoic acid 0.1 mole of 2,6-di-t-butylphenol, 0.12 mole of chloroform, 1 mole of 2-butanone, and 0.003 mole of benzyltriethylammonium were mixed in the 500 ml three-neck reactor while stirring. 0.5 mole of powdered sodium hydroxide was added in small portions during a 30 minute period. After the addition, the reaction temperature was slowly raised to 10° and stirred overnight. 200 ml of 4N HCl then was added slowly. The resulting 2 layers were separated. The aqueous layer was extracted twice with 50 ml methylene chloride and this was combined with the organic layer, then dried with sodium sulfate and concentrated. The residue was washed with hexanes to obtain crystals in 80% yield. The melting point was 141°–144° C.; molecular weight 306; carbon-calculated 74.47%, found 74.60%; hydrogen-calculated 9.87%, found 9.89%.

EXAMPLE III

α-(3,5-Di-t-butyl-4-hydroxyphenyl)cyclohexanecarboxylic acid 0.1 mole of 2,6-t-butylphenol, 0.12 mole of chloroform, 1.0 mole of cyclohexanone, and 0.003 mole of benzyltriethylammonium chloride were mixed in the 500 ml three-neck reactor while stirring. 0.5 mole of powdered sodium hydroxide was added in small portions during a 30 minute period. After the addition, the reaction temperature was slowly raised to 10° C. and stirred overnight. 200 ml of 4N HCl then was added slowly. The resulting 2 layers were separated. The aqueous layer was extracted twice with 50 ml methylene chloride and this was combined with the organic layer, dried with sodium sulfate and concentrated. The residue was washed with hexane to obtain crystals in 80% yield. The melting point was 187°–191° C.; molecular weight 332; carbon-calculated 75.86%, found 73.35%; hydrogen-calculated 9.70%, found 9.59%.

EXAMPLE IV 2-(3-methyl-5-t-butyl-4-hydroxyphenol)-2-propionic acid 0.1 mole of 2-methyl,5-t-butylphenol, 0.12 mole of chloroform, 0.15 mole of acetone, and 0.003 mole of benzyltriethylammomium chloride were mixed with 100 ml methylene chloride in a 500 ml three-neck reactor equipped with a circulating cold bath. With stirring, 0.5 mole of powdered sodium hydroxide was added in small portions during a 30 minute period. After the addition, the reaction temperature was slowly raised to 10° C. and stirred overnight. 200 ml of 4N HCl was added slowly. The two layers were separated. The aqueous layer was extracted twice with 50 ml of methylene chloride and this extract was combined with the organic layer. This was dried with sodium sulfate and concentrated. The residue was washed with hexane to obtain crystals in low yield. The melting point was 160°–163° C.; molecular weight 250; carbon-calculated 71.97%, found 71.94%, hydrogen-calculated 8.86%, found 8.86%.

These 3,5-dialkyl-4-hydroxyphenyl-substituted acetic acids may be used as stabilizers to protect organic materials subject to attack and degradation by oxygen, heat and light, where water solubility is not a problem. In many applications there is no exposure of the stabilized material to water and 3,5-dialkyl-4-hydroxyphenyl-$\alpha,\alpha'$-dialkyl acetic acids, for example, may be used as excellent stabilizers. Such materials that may be so stabilized include polymers, especially polyolefins, cellulosic materials; natural rubbers, synthetic unsaturated diolefin derived elastomers, the vinylidene polymers made from unsaturated polymerizable monomers having at least one terminal $CH_2<$ group, including styrene, vinyl chloride and the alkyl acrylates, polycarbonates, polyurethanes, nylon type materials, epoxy resins, waxes, synthetic and petroleum-derived lubricating oils and greases; animal oils such as, for example, fat, tallow, lard, codliver oil, sperm oil; vegetable oils such as castor, linseed, peanut, palm, cotton seed, and the like; fuel oil, diesel oil, gasoline and the like.

A particularly useful application of these 3,5-dialkyl-4-hydroxyphenol-substituted acetic acids is to make esters therefrom that are also of utility as stabilizers for organic materials subject to degradation. In one Example, methyl-$\alpha$-(3,5-di-t-butyl-4-hydroxyphenol-$\alpha',\alpha''$-dimethyl acetate was prepared as follows:

EXAMPLE V 0.01 mole of 3,5-di-t-butyl-4-hydroxyphenyl-$\alpha,\alpha'$-dimethyl acetic acid, 0.02 mole of iodomethane, 20 ml of dimethyl formamide and 0.04 moles of potassium carbonate were mixed together and stirred at ambient temperature for 4 hours. The reaction mixture was filtered and concentrated to dryness to obtain a white powder, the methyl-$\alpha$-(3,5-di-t-butyl-4-hydroxyphenyl)-$\alpha',\alpha''$-dimethyl acetate.

Test samples of methyl-$\alpha$-(3,5-di-t-butyl-4-hydroxyphenol-$\alpha',\alpha''$-dimethyl acetate in polypropylene were prepared by mixing the stabilizer compounds with polypropylene in a Brabender Plasticorder fitted with a Cam-Head (mixing chamber). The polypropylene was first masticated for 1½ minutes at 190° C. Then the stabilizer was added, followed by 3 minutes additional mixing. The mass was removed and pressed into 20 mil thick sheets. From these sheets 1"×1" plaques were cut for oven aging.

Thermal/oxidative stability (oven aging) testing consisted of aging the samples in triplicate in an air-circulating oven at 125° C. The time to catastrophic crumbling (failure) of the plaque was measured and reported as days to failure.

A blank (control) failed after only 2 days. Samples containing 0.1 weight parts of methyl-$\alpha$-(3,5-di-t-butyl-4-hydroxyphenyl)-$\alpha',\alpha''$-dimethyl acetate failed after 5 days. A sample containing 0.05 weight parts of the methyl-$\alpha$-(3,5-di-t-butyl-4-hydroxyphenyl-$\alpha',\alpha''$-dimethyl acetate and 0.05 weight part of 2,2',2"-tris[3(3,5-di-t-butyl-4-hydroxyphenyl)propionyloxy]ethyl isocyanurate did not fail until 78 days.

I claim:

1. 3,5-dialkyl-4-hydroxyphenyl-substituted acetic acids having the formula

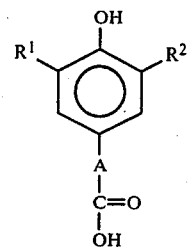

wherein $R^1$ and $R^2$ are alkyl or cycloalkyl groups containing 1 to 12 carbon atoms, alkylcycloalkyls and aryl or alkaryl groups wherein the alkyl groups contain 1 to 8 carbon atoms, and A is (1) an alkyl group having the formula

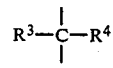

wherein $R^3$ and $R^4$ are alkyl groups containing 1 to 18 carbon atoms, or (2) a cycloalkyl group containing 5 to 12 carbon atoms, and alkaryl groups wherein the alkyl groups contain 1 to 8 carbon atoms.

2. 3,5-dialkyl-4-hydroxyphenyl-substituted acids of claim 1 wherein $R^1$ contains 1 to 8 carbon atoms, $R^2$ contains 1 to 5 carbon atoms, $R^3$ and $R^4$ contain 1 to 8 carbon atoms and (2) is cyclohexyl, methylcyclohexyl, cycloheptyl, or dicyclohexyl.

3. 3,5-dialkyl-4-hydroxyphenyl-$\alpha,\alpha'$-dialkyl acetic acids of claim 2 wherein at least one of $R^1$ and $R^2$ is t-butyl or t-amyl, and $R^3$ and $R^4$ are alkyl radicals containing 1 to 4 carbon atoms.

4. 2-(3,5-di-t-butyl-4-hydroxyphenyl)-2-methyl propionic acid of claim 3.

5. 2-(3,5-di-t-butyl-4-hydroxyphenyl)-2-methylbutanoic acid of claim 3.

6. $\alpha$-(3,5-di-t-butyl-hydroxyphenyl)-cyclohexanecarboxylic acid of claim 3.

7. 2-(3-methyl-5-t-butyl-4-hydroxyphenyl)-2-propanoic acid of claim 3.

8. A process for preparing 3,5-dialkyl-4-hydroxyphenyl-substituted acetic acids having the formula

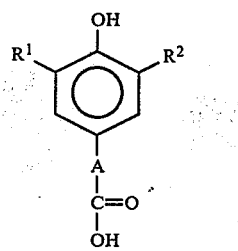

wherein $R^1$ and $R^2$ are alkyl or cycloalkyl groups containing 1 to 12 carbon atoms, alkylcycloalkyls and aryl or alkaryl groups wherein the alkyl groups contain 1 to 8 carbon atoms, and A is (1) an alkyl group having the formula

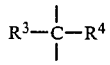

wherein $R^3$ and $R^4$ are alkyl groups containing 1 to 18 carbon atoms, or (2) a cycloalkyl groups containing 5 to 12 carbon atoms, and alkaryl groups wherein the alkyl groups contain 1 to 8 carbon atoms, comprising reacting together a 2,6-dialkylphenol having the formula

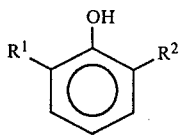

wherein $R^1$ and $R^2$ have the meanings above, a ketone selected from the group consisting of dialkyl ketones, cycloalakanones, alkcycloalkanones, and alkaryl ketones wherein the alkyl groups contain 1 to 18 carbon atoms, a haloform selected from the group consisting of chloroform and bromoform, and an alkali metal hydroxide.

9. A process of claim 8 wherein $R^1$ contains 1 to 8 carbon atoms and $R^2$ contains 1 to 5 carbon atoms, the ketone is a dialkyl ketone of the formula

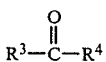

wherein $R^3$ and $R^4$ are alkyl radicals containing 1 to 8 carbon atoms, cyclopentanone, cyclohexanone, cycloheptanone and alkyl derivatives thereof wherein the alkyl groups contain 1 to 4 carbon atoms, the haloform is chloroform and the alkali metal hydroxide is sodium hydroxide or potassium hydroxide.

10. A process of claim 9 wherein at least one of $R^1$ and $R^2$ are t-butyl or t-amyl, $R^3$ and $R^4$ are alkyl radicals containing 1 to 4 carbon atoms, and the reaction is conducted in a polar solvent.

11. A process of claim 10 wherein the polar solvent is an excess of the ketone.

12. A process of claim 10 wherein the reaction is conducted in the presence of a catalytic amount of an onium salt having the formula $(R_4Y)X$ wherein R is a monovalent hydrocarbon radical, Y is derived from a group VA or VIA element, and X is a salt anion.

13. A process of claim 12 to make 2-(3,5-di-t-butyl-4-hydroxyphenyl)-2-methyl propionic acid comprising reacting together 2,6-di-t-butylphenol, chloroform, acetone and benzyltriethylammonium chloride in methyl chloride with sodium hydroxide in a molar ratio of one mole of 2,6-di-t-butylphenol, about 1 to 2 moles of acetone, about 1 to 1.5 moles of chloroform, 0.001 to about 0.01 moles of benzyltriethylammonium chloride, about 4 to 8 moles of sodium hydroxide and about 10 to 20 moles of methylene chloride, at a temperature in the range of about 0° C. to about 20° C.

14. A process of claim 12 to make 2-(3,5-di-t-butyl-4-hydroxyphenyl)-2-methyl butanoic acid comprising reacting together 2,6-di-t-butylphenol, chloroform, 2-butanone and benzyltriethylammonium chloride in methylene chloride with sodium hydroxide in a molar ratio of one mole of 2,6-di-t-butylphenol, about 5 to 15 moles of 2-butanone, about 1 to 1.5 moles of chloroform, 0.001 to about 0.01 moles of benzyltriethylammonium chloride, and about 4 to 8 moles of sodium hydroxide, at a temperature in the range of about 0° C. to about 20° C.

15. A process of claim 12 to make 2-(3,5-di-t-butyl-4-hydroxyphenyl)-cyclohexanecarboxylic acid comprising reacting together 2,6-di-t-butylphenol, chloroform, cyclohexanone and benzyltriethylammonium chloride in methylene chloride with sodium hydroxide in a molar ratio of one mole of 2,6-di-t-butylphenol, about 5 to 15 moles of cyclohexanone, about 1 to 1.5 moles of chloroform, 0.001 to about 0.01 moles of benzyltriethylammonium chloride, and about 4 to 8 moles of sodium hydroxide, at a temperature in the range of about 0° C. to about 20° C.

16. A process of claim 12 to make 2-(3-methyl,5-t-butyl-4-hydroxyphenyl)-2-propionic acid comprising reacting together 2-methyl,6-di-t-butylphenol, chloroform, acetone and benzyltriethylammonium chloride in methyl chloride with sodium hydroxide in a molar ratio of one mole of 2,6-di-t-butylphenol, about 1 to 2 moles of acetone, about 1 to 1.5 moles of chloroform, 0.001 to about 0.01 moles of benzyltriethylammonium chloride, about 4 to 8 moles of sodium hydroxide and about 10 to 20 moles of methylene chloride, at a temperature in the range of about 0° C. to about 20° C.

* * * * *